United States Patent
Jennings (10) Patent No.: US 8,834,419 B2
(45) Date of Patent: Sep. 16, 2014

(54) REUSABLE AUTO-INJECTOR

(75) Inventor: Douglas Ivan Jennings, Royston (GB)

(73) Assignee: Cilag GmbH International, Zug (CH)

( * ) Notice: Subject to any disclaimer, the term of this patent is extended or adjusted under 35 U.S.C. 154(b) by 393 days.

(21) Appl. No.: 12/997,660

(22) PCT Filed: Jun. 10, 2009

(86) PCT No.: PCT/GB2009/001445
§ 371 (c)(1),
(2), (4) Date: Dec. 13, 2010

(87) PCT Pub. No.: WO2009/153540
PCT Pub. Date: Dec. 23, 2009

(65) Prior Publication Data
US 2011/0092954 A1    Apr. 21, 2011

(30) Foreign Application Priority Data

Jun. 19, 2008   (GB) .................................. 0811349.0

(51) Int. Cl.
*A61M 5/20*   (2006.01)
*A61M 5/178*  (2006.01)
*A61M 5/32*   (2006.01)

(52) U.S. Cl.
CPC ....... *A61M 5/2033* (2013.01); *A61M 2005/206* (2013.01); *A61M 5/1782* (2013.01); *A61M 5/326* (2013.01); *A61M 5/3287* (2013.01)
USPC ........................................................ 604/139

(58) Field of Classification Search
USPC .................. 604/139, 150, 186, 207
See application file for complete search history.

(56) References Cited

U.S. PATENT DOCUMENTS

| | | | |
|---|---|---|---|
| 1,845,036 A | 2/1932 | Busher |
| 2,019,382 A | 10/1935 | Aronson |
| 2,531,267 A | 11/1950 | Harisch |
| 2,764,977 A | 10/1956 | Ferguson |
| 2,828,742 A | 4/1958 | Ashkenaz |
| 3,320,955 A | 5/1967 | Sarnoff |
| 3,329,146 A | 7/1967 | Waldman |
| 3,543,603 A | 12/1970 | Gley |
| 3,656,472 A | 4/1972 | Moura |
| 3,702,608 A | 11/1972 | Tibbs |

(Continued)

FOREIGN PATENT DOCUMENTS

| | | |
|---|---|---|
| CH | 518102 A | 1/1972 |
| CN | 2059579 U | 7/1990 |

(Continued)

OTHER PUBLICATIONS

European Search Report dated Aug. 3, 2011; Application No. 11170040.

(Continued)

*Primary Examiner* — Kevin C Sirmons
*Assistant Examiner* — Deanna K Hall (57) ABSTRACT

An injection device comprises a first sub-assembly comprising a chamber for holding a fluid and a transfer assembly moveably disposed within the chamber. The chamber comprises an exit aperture and an inner surface and the transfer assembly has an outer surface substantially in contact with the inner surface about its perimeter. The transfer assembly is adapted to transfer fluid into the chamber when the transfer assembly is moved within the chamber.

11 Claims, 4 Drawing Sheets

(56) References Cited

U.S. PATENT DOCUMENTS

| | | |
|---|---|---|
| 3,742,948 A | 7/1973 | Post et al. |
| 3,797,488 A | 3/1974 | Hurschman et al. |
| 3,797,489 A | 3/1974 | Sarnoff |
| 3,880,163 A | 4/1975 | Ritterskamp |
| 3,976,069 A | 8/1976 | Ong |
| 4,165,739 A | 8/1979 | Doherty et al. |
| 4,180,070 A | 12/1979 | Genese |
| 4,185,628 A | 1/1980 | Kopfer |
| 4,194,505 A | 3/1980 | Schmitz |
| 4,222,380 A | 9/1980 | Terayama |
| 4,231,368 A | 11/1980 | Becker |
| 4,236,516 A | 12/1980 | Nilson |
| 4,299,238 A | 11/1981 | Baidwan et al. |
| 4,378,015 A | 3/1983 | Wardlaw |
| 4,394,863 A | 7/1983 | Bartner |
| 4,403,989 A | 9/1983 | Christensen et al. |
| 4,407,283 A | 10/1983 | Reynolds |
| 4,425,120 A | 1/1984 | Sampson et al. |
| 4,430,082 A | 2/1984 | Schwabacher |
| 4,521,237 A | 6/1985 | Logothetis |
| 4,561,856 A | 12/1985 | Cochran |
| 4,636,201 A | 1/1987 | Ambrose et al. |
| 4,639,250 A | 1/1987 | Rycroft |
| 4,642,099 A | 2/1987 | Phillips et al. |
| 4,676,530 A | 6/1987 | Nordgren et al. |
| 4,744,786 A | 5/1988 | Hooven et al. |
| 4,787,891 A | 11/1988 | Levin et al. |
| 4,874,383 A | 10/1989 | McNaughton |
| 4,874,384 A | 10/1989 | Nunez |
| 4,929,232 A | 5/1990 | Sweeney et al. |
| 4,969,870 A | 11/1990 | Kramer et al. |
| 4,988,339 A | 1/1991 | Vadher |
| 5,009,646 A | 4/1991 | Sudo et al. |
| 5,026,349 A | 6/1991 | Schmitz et al. |
| 5,057,079 A | 10/1991 | Tiemann et al. |
| 5,092,842 A | 3/1992 | Bechtold et al. |
| 5,098,400 A | 3/1992 | Crouse et al. |
| 5,112,119 A | 5/1992 | Cooke et al. |
| 5,114,406 A | 5/1992 | Gabriel et al. |
| 5,122,119 A | 6/1992 | Lucas |
| 5,137,516 A | 8/1992 | Rand et al. |
| 5,141,496 A | 8/1992 | Dalto et al. |
| 5,147,325 A | 9/1992 | Mitchell et al. |
| 5,156,599 A | 10/1992 | Ranford et al. |
| 5,176,643 A | 1/1993 | Kramer et al. |
| 5,190,526 A | 3/1993 | Murray et al. |
| 5,242,416 A | 9/1993 | Hutson |
| 5,250,026 A | 10/1993 | Ehrlich et al. |
| 5,250,037 A | 10/1993 | Bitdinger |
| 5,263,933 A | 11/1993 | Novacek et al. |
| 5,267,963 A | 12/1993 | Bachynsky |
| 5,271,744 A | 12/1993 | Kramer et al. |
| 5,295,965 A | 3/1994 | Wilmot |
| 5,300,030 A | 4/1994 | Crossman et al. |
| 5,312,364 A | 5/1994 | Jacobs |
| 5,330,081 A | 7/1994 | Davenport |
| 5,330,430 A | 7/1994 | Sullivan |
| 5,358,489 A | 10/1994 | Wyrick |
| 5,364,369 A | 11/1994 | Reynolds |
| 5,368,577 A | 11/1994 | Teoh et al. |
| 5,372,586 A | 12/1994 | Haber et al. |
| 5,391,151 A | 2/1995 | Wilmot |
| 5,405,362 A | 4/1995 | Kramer et al. |
| 5,411,488 A | 5/1995 | Pagay et al. |
| 5,425,715 A | 6/1995 | Dalling et al. |
| 5,451,210 A | 9/1995 | Kramer et al. |
| 5,478,316 A | 12/1995 | Bitdinger et al. |
| 5,480,387 A | 1/1996 | Gabriel et al. |
| 5,487,732 A | 1/1996 | Jeffrey |
| 5,489,256 A | 2/1996 | Adair |
| 5,503,627 A | 4/1996 | McKinnon et al. |
| 5,514,097 A | 5/1996 | Knauer |
| 5,520,653 A | 5/1996 | Reilly et al. |
| 5,540,660 A | 7/1996 | Jenson et al. |
| 5,540,666 A | 7/1996 | Barta et al. |
| 5,540,709 A | 7/1996 | Ramel |
| 5,567,160 A | 10/1996 | Massino |
| 5,569,191 A | 10/1996 | Meyer |
| 5,569,192 A | 10/1996 | van der Wal |
| 5,575,777 A | 11/1996 | Cover et al. |
| 5,599,302 A | 2/1997 | Lilley et al. |
| 5,599,309 A | 2/1997 | Marshall et al. |
| 5,607,395 A | 3/1997 | Ragsdale et al. |
| 5,609,577 A | 3/1997 | Haber et al. |
| 5,609,584 A | 3/1997 | Gettig et al. |
| 5,611,785 A | 3/1997 | Mito et al. |
| 5,637,094 A | 6/1997 | Stewart, Jr. et al. |
| 5,645,536 A | 7/1997 | Whisson |
| 5,647,845 A | 7/1997 | Haber et al. |
| 5,658,259 A | 8/1997 | Pearson et al. |
| 5,665,071 A | 9/1997 | Wyrick |
| 5,681,291 A | 10/1997 | Galli |
| 5,697,908 A | 12/1997 | Imbert et al. |
| 5,702,367 A | 12/1997 | Cover et al. |
| 5,704,911 A | 1/1998 | Parsons |
| 5,709,662 A | 1/1998 | Olive et al. |
| 5,713,866 A | 2/1998 | Wilmot |
| 5,748,316 A | 5/1998 | Wakabayashi et al. |
| 5,779,668 A | 7/1998 | Grabenkort |
| 5,779,677 A | 7/1998 | Frezza |
| 5,807,334 A | 9/1998 | Hodosh et al. |
| 5,817,058 A | 10/1998 | Shaw |
| 5,827,262 A | 10/1998 | Neftel et al. |
| 5,843,036 A | 12/1998 | Olive et al. |
| 5,855,839 A | 1/1999 | Brunel |
| 5,865,795 A | 2/1999 | Schiff et al. |
| 5,865,804 A | 2/1999 | Bachynsky |
| 5,868,711 A | 2/1999 | Kramer et al. |
| 5,879,327 A | 3/1999 | Moreau DeFarges et al. |
| 5,913,843 A | 6/1999 | Jentzen |
| 5,928,205 A | 7/1999 | Marshall |
| 5,954,738 A | 9/1999 | LeVaughn et al. |
| 5,957,897 A | 9/1999 | Jeffrey |
| 5,960,797 A | 10/1999 | Kramer et al. |
| 5,997,513 A | 12/1999 | Smith et al. |
| 6,007,515 A | 12/1999 | Epstein et al. |
| 6,015,438 A | 1/2000 | Shaw |
| 6,017,330 A | 1/2000 | Hitchins et al. |
| 6,036,675 A | 3/2000 | Thorne et al. |
| 6,045,534 A | 4/2000 | Jacobsen et al. |
| 6,068,614 A | 5/2000 | Kimber et al. |
| 6,077,247 A | 6/2000 | Marshall et al. |
| 6,083,197 A | 7/2000 | Umbaugh |
| 6,086,562 A | 7/2000 | Jacobsen et al. |
| 6,090,070 A * | 7/2000 | Hager et al. .................. 604/131 |
| 6,090,078 A | 7/2000 | Erskine |
| 6,090,897 A | 7/2000 | Akasaki et al. |
| 6,099,503 A | 8/2000 | Stradella |
| 6,099,504 A | 8/2000 | Gross et al. |
| 6,123,684 A | 9/2000 | Deboer et al. |
| 6,139,534 A | 10/2000 | Niedospial, Jr. et al. |
| 6,159,161 A | 12/2000 | Hodosh |
| 6,159,181 A | 12/2000 | Crossman et al. |
| 6,159,184 A | 12/2000 | Perez et al. |
| 6,162,199 A | 12/2000 | Geringer |
| 6,171,276 B1 | 1/2001 | Adam et al. |
| 6,179,812 B1 | 1/2001 | Botich et al. |
| 6,186,980 B1 | 2/2001 | Brunel |
| 6,190,363 B1 | 2/2001 | Gabbard et al. |
| 6,193,696 B1 | 2/2001 | Jansen et al. |
| 6,203,530 B1 | 3/2001 | Stewart, Sr. |
| 6,209,738 B1 | 4/2001 | Jansen et al. |
| 6,221,044 B1 | 4/2001 | Greco |
| 6,258,068 B1 | 7/2001 | Kirchhofer et al. |
| 6,270,479 B1 | 8/2001 | Bergens et al. |
| 6,280,421 B1 | 8/2001 | Kirchhofer et al. |
| 6,290,683 B1 | 9/2001 | Erez et al. |
| 6,293,925 B1 | 9/2001 | Safabash et al. |
| 6,317,939 B1 | 11/2001 | Malin |
| 6,330,960 B1 | 12/2001 | Faughey et al. |
| 6,332,875 B2 | 12/2001 | Inkpen et al. |
| 6,371,939 B2 | 4/2002 | Bergens et al. |
| 6,371,959 B1 | 4/2002 | Trice |
| 6,387,078 B1 | 5/2002 | Gillespie, III |

(56) References Cited

U.S. PATENT DOCUMENTS

| | | |
|---|---|---|
| 6,391,003 B1 | 5/2002 | Lesch, Jr. |
| 6,419,658 B1 | 7/2002 | Restelli et al. |
| 6,428,528 B2 | 8/2002 | Sadowski et al. |
| 6,447,480 B1 | 9/2002 | Brunel |
| 6,454,743 B1 | 9/2002 | Weber |
| 6,454,746 B1 | 9/2002 | Bydion et al. |
| 6,461,333 B1 | 10/2002 | Frezza |
| 6,517,517 B1 | 2/2003 | Farrugia et al. |
| 6,537,252 B1 | 3/2003 | Hansen |
| 6,544,234 B1 | 4/2003 | Gabriel |
| 6,565,540 B1 | 5/2003 | Perouse et al. |
| 6,565,553 B2 | 5/2003 | Sadowski et al. |
| 6,569,115 B1 | 5/2003 | Barker et al. |
| 6,569,123 B2 | 5/2003 | Alchas et al. |
| 6,569,124 B1 | 5/2003 | Perouse |
| 6,572,581 B1 | 6/2003 | Landua |
| 6,575,939 B1 | 6/2003 | Brunel |
| 6,585,702 B1 | 7/2003 | Brunel |
| 6,589,210 B1 | 7/2003 | Rolfe |
| 6,595,957 B1 | 7/2003 | Griffiths et al. |
| 6,595,962 B1 | 7/2003 | Perthu |
| 6,599,272 B1 | 7/2003 | Hjertman et al. |
| 6,607,508 B2 | 8/2003 | Knauer |
| 6,607,510 B2 | 8/2003 | Landau |
| 6,613,022 B1 | 9/2003 | Doyle |
| 6,620,137 B2 | 9/2003 | Kirchhofer et al. |
| 6,638,256 B2 | 10/2003 | Jansen et al. |
| 6,641,554 B2 | 11/2003 | Landau |
| 6,641,560 B1 | 11/2003 | Bechtold et al. |
| 6,641,565 B1 | 11/2003 | Lavi et al. |
| 6,645,170 B2 | 11/2003 | Landua |
| 6,645,181 B1 | 11/2003 | Lavi et al. |
| 6,648,835 B1 | 11/2003 | Shemesh |
| 6,648,850 B2 | 11/2003 | Landau |
| 6,656,163 B1 | 12/2003 | Marshall et al. |
| 6,673,049 B2 | 1/2004 | Hommann et al. |
| 6,676,630 B2 | 1/2004 | Landau et al. |
| 6,689,093 B2 | 2/2004 | Landau et al. |
| 6,692,469 B1 | 2/2004 | Weekes et al. |
| 6,699,220 B2 | 3/2004 | Rolfe |
| 6,740,062 B2 | 5/2004 | Hjertman |
| 6,743,199 B2 | 6/2004 | Shue et al. |
| 6,743,203 B1 | 6/2004 | Pickhard et al. |
| 6,746,429 B2 | 6/2004 | Sadowski et al. |
| 6,767,336 B1 | 7/2004 | Kaplan |
| 6,770,056 B2 | 8/2004 | Price et al. |
| 6,776,777 B2 | 8/2004 | Barrelle |
| 6,783,509 B1 | 8/2004 | Landau et al. |
| 6,793,161 B1 | 9/2004 | Fujita et al. |
| 6,796,967 B2 | 9/2004 | Jensen |
| 6,811,548 B2 | 11/2004 | Jeffrey |
| 6,846,303 B2 | 1/2005 | Eakins et al. |
| 6,875,205 B2 | 4/2005 | Leinsing |
| 6,890,319 B1 | 5/2005 | Crocker |
| 6,899,698 B2 | 5/2005 | Sams |
| 6,932,793 B1 | 8/2005 | Marshall et al. |
| 6,939,319 B1 | 9/2005 | Anstead et al. |
| 6,979,316 B1 | 12/2005 | Rubin et al. |
| 7,066,907 B2 | 6/2006 | Crossman et al. |
| 7,097,071 B2 | 8/2006 | Anderson et al. |
| 7,097,634 B2 | 8/2006 | Gilbert |
| 7,118,553 B2 | 10/2006 | Scherer |
| 7,156,823 B2 | 1/2007 | Landau et al. |
| 7,160,913 B2 | 1/2007 | Schneider |
| 7,294,122 B2 | 11/2007 | Kubo et al. |
| 7,354,427 B2 | 4/2008 | Fangrow |
| RE40,428 E | 7/2008 | Keane et al. |
| 7,442,185 B2 | 10/2008 | Amark et al. |
| 7,470,258 B2 | 12/2008 | Barker et al. |
| 7,507,227 B2 | 3/2009 | Fangrow |
| 7,510,547 B2 | 3/2009 | Fangrow |
| 7,510,548 B2 | 3/2009 | Fangrow |
| 7,513,895 B2 | 4/2009 | Fangrow |
| 7,534,238 B2 | 5/2009 | Fangrow |
| 7,547,300 B2 | 6/2009 | Fangrow |
| 7,569,043 B2 | 8/2009 | Fangrow |
| 7,618,396 B2 | 11/2009 | Slate et al. |
| 7,635,356 B2 | 12/2009 | Stamp |
| 7,645,271 B2 | 1/2010 | Fangrow |
| 7,654,995 B2 | 2/2010 | Warren et al. |
| 7,658,733 B2 | 2/2010 | Fangrow |
| 7,678,333 B2 | 3/2010 | Reynolds et al. |
| 7,682,345 B2 | 3/2010 | Savage |
| 7,717,879 B2 | 5/2010 | Mansouri |
| 7,744,561 B2 | 6/2010 | Stamp |
| 7,759,654 B2 | 7/2010 | Yan et al. |
| 7,794,434 B2 | 9/2010 | Mounce et al. |
| 7,799,009 B2 | 9/2010 | Niedospial, Jr. et al. |
| 7,811,262 B2 | 10/2010 | Moberg et al. |
| 7,828,764 B2 | 11/2010 | Moberg et al. |
| 7,871,397 B2 | 1/2011 | Schraga |
| 7,879,010 B2 | 2/2011 | Hunn et al. |
| 7,883,499 B2 | 2/2011 | Fangrow |
| 7,959,715 B2 | 6/2011 | Kavazov et al. |
| 7,972,321 B2 | 7/2011 | Fangrow |
| 8,100,154 B2 | 1/2012 | Reynolds et al. |
| 8,177,768 B2 | 5/2012 | Leinsing |
| 8,277,414 B2 | 10/2012 | Barrow-Williams et al. |
| 8,313,463 B2 | 11/2012 | Barrow-Williams et al. |
| 8,409,138 B2 | 4/2013 | James et al. |
| 8,491,530 B2 | 7/2013 | Maritan |
| 2001/0005781 A1 | 6/2001 | Bergens et al. |
| 2001/0021828 A1 | 9/2001 | Fischer et al. |
| 2001/0037089 A1 | 11/2001 | Domici, Jr. |
| 2001/0049496 A1 | 12/2001 | Kirchhofer et al. |
| 2001/0051789 A1 | 12/2001 | Parsons |
| 2002/0032412 A1 | 3/2002 | Riemelmoser |
| 2002/0072709 A1 | 6/2002 | Sadowski et al. |
| 2002/0095120 A1 | 7/2002 | Larsen et al. |
| 2002/0151839 A1 | 10/2002 | Landau |
| 2002/0161334 A1 | 10/2002 | Castellano et al. |
| 2002/0165500 A1 | 11/2002 | Bechtold et al. |
| 2002/0173752 A1 | 11/2002 | Polzin |
| 2002/0183690 A1 | 12/2002 | Arnisolle |
| 2003/0036679 A1 | 2/2003 | Kortenbach |
| 2003/0036725 A1 | 2/2003 | Lavi et al. |
| 2003/0050609 A1 | 3/2003 | Sams |
| 2003/0060773 A1 | 3/2003 | Nguyen |
| 2003/0065286 A1 | 4/2003 | Landau |
| 2003/0078546 A1 | 4/2003 | Jensen |
| 2003/0088207 A1 | 5/2003 | Rogatchev et al. |
| 2003/0088216 A1 | 5/2003 | Py |
| 2003/0093030 A1 | 5/2003 | Landau |
| 2003/0093035 A1 | 5/2003 | Mohammed |
| 2003/0093036 A1 | 5/2003 | Crossman et al. |
| 2003/0105430 A1 | 6/2003 | Lavi et al. |
| 2003/0109833 A1 | 6/2003 | Sharpe |
| 2003/0120212 A1 | 6/2003 | Dedig et al. |
| 2003/0120222 A1 | 6/2003 | Vaillancourt |
| 2003/0121815 A1 | 7/2003 | Bergeron et al. |
| 2003/0135157 A1 | 7/2003 | Saulenas et al. |
| 2003/0181859 A1 | 9/2003 | Brunel |
| 2003/0184973 A1 | 10/2003 | Nagata et al. |
| 2003/0196928 A1 | 10/2003 | Parsons |
| 2003/0199814 A1 | 10/2003 | Parsons et al. |
| 2003/0208164 A1 | 11/2003 | Botich et al. |
| 2003/0212362 A1 | 11/2003 | Roser |
| 2003/0212370 A1 | 11/2003 | Barrelle |
| 2003/0212380 A1 | 11/2003 | Barrelle |
| 2003/0225368 A1 | 12/2003 | Landau et al. |
| 2003/0229308 A1 | 12/2003 | Tsals et al. |
| 2003/0233070 A1 | 12/2003 | De La serna et al. |
| 2003/0236502 A1 | 12/2003 | De La Serna et al. |
| 2003/0236504 A1 | 12/2003 | Chen |
| 2004/0002684 A1 | 1/2004 | Lopez |
| 2004/0015134 A1 | 1/2004 | Lavi et al. |
| 2004/0019326 A1 | 1/2004 | Gilbert et al. |
| 2004/0024367 A1 | 2/2004 | Gilbert |
| 2004/0039336 A1 | 2/2004 | Amark et al. |
| 2004/0039366 A1 | 2/2004 | MacLeod |
| 2004/0069044 A1 | 4/2004 | Lavi et al. |
| 2004/0087897 A1 | 5/2004 | Hjertman |
| 2004/0102740 A1 | 5/2004 | Meloul |
| 2004/0111054 A1 | 6/2004 | Landau et al. |

(56) References Cited

U.S. PATENT DOCUMENTS

| | | |
|---|---|---|
| 2004/0111057 A1 | 6/2004 | Wilkinson |
| 2004/0133159 A1 | 7/2004 | Haider et al. |
| 2004/0138618 A1 | 7/2004 | Mazzoni |
| 2004/0143224 A1 | 7/2004 | Field et al. |
| 2004/0153033 A1 | 8/2004 | Mazzoni |
| 2004/0225262 A1 | 11/2004 | Fathallah et al. |
| 2004/0243065 A1 | 12/2004 | McConnell et al. |
| 2005/0011780 A1 | 1/2005 | Simon et al. |
| 2005/0020979 A1 | 1/2005 | Westbye et al. |
| 2005/0020980 A1 | 1/2005 | Inoue et al. |
| 2005/0027255 A1 | 2/2005 | Lavi et al. |
| 2005/0033234 A1 | 2/2005 | Sadowski et al. |
| 2005/0035029 A1 | 2/2005 | Grob |
| 2005/0040716 A1 | 2/2005 | Schmid et al. |
| 2005/0049550 A1 | 3/2005 | Kirchhofer et al. |
| 2005/0049561 A1 | 3/2005 | Hommann et al. |
| 2005/0075608 A1 | 4/2005 | Holdgate et al. |
| 2005/0085776 A1 | 4/2005 | Hommann et al. |
| 2005/0090782 A1 | 4/2005 | Marshall et al. |
| 2005/0097238 A1 | 5/2005 | Oomori et al. |
| 2005/0101919 A1 | 5/2005 | Brunnberg |
| 2005/0124940 A1 | 6/2005 | Martin et al. |
| 2005/0125019 A1 | 6/2005 | Kudna et al. |
| 2005/0137523 A1 | 6/2005 | Wyatt et al. |
| 2005/0168855 A1 | 8/2005 | Fanelli et al. |
| 2005/0203466 A1 | 9/2005 | Hommann et al. |
| 2005/0209554 A1 | 9/2005 | Landau |
| 2005/0215941 A1 | 9/2005 | Bernard et al. |
| 2005/0215951 A1 | 9/2005 | Saulenas et al. |
| 2005/0222539 A1 | 10/2005 | Gonzales et al. |
| 2005/0261633 A1 | 11/2005 | Khalaj |
| 2005/0261634 A1 | 11/2005 | Karlsson |
| 2005/0267403 A1 | 12/2005 | Landau et al. |
| 2005/0273054 A1 | 12/2005 | Asch |
| 2005/0273055 A1 | 12/2005 | Harrison et al. |
| 2005/0277885 A1 | 12/2005 | Scherer |
| 2005/0277886 A1 | 12/2005 | Hommann et al. |
| 2005/0277896 A1 | 12/2005 | Messerli et al. |
| 2005/0288633 A1 | 12/2005 | Jeffrey |
| 2006/0016835 A1 | 1/2006 | Perry |
| 2006/0030819 A1 | 2/2006 | Young et al. |
| 2006/0036216 A1 | 2/2006 | Rimlinger et al. |
| 2006/0036217 A1 | 2/2006 | Doyle |
| 2006/0069345 A1 | 3/2006 | Anderson et al. |
| 2006/0069348 A1 | 3/2006 | Parker et al. |
| 2006/0069350 A1 | 3/2006 | Buenger et al. |
| 2006/0079834 A1 | 4/2006 | Tennican et al. |
| 2006/0100588 A1 | 5/2006 | Brunnberg et al. |
| 2006/0106295 A1 | 5/2006 | Jais et al. |
| 2006/0161111 A1 | 7/2006 | Potter et al. |
| 2006/0178631 A1 | 8/2006 | Gillespie et al. |
| 2006/0184119 A1 | 8/2006 | Remde et al. |
| 2006/0184137 A1 | 8/2006 | Reynolds |
| 2006/0189938 A1 | 8/2006 | Hommann et al. |
| 2006/0200093 A1 | 9/2006 | Lopez |
| 2006/0206060 A1 | 9/2006 | Lopez |
| 2006/0224124 A1 | 10/2006 | Scherer |
| 2006/0229572 A1 | 10/2006 | Lopez |
| 2006/0258986 A1 | 11/2006 | Hunter et al. |
| 2006/0258990 A1 | 11/2006 | Weber |
| 2006/0270986 A1 | 11/2006 | Hommann et al. |
| 2007/0027430 A1 | 2/2007 | Hommann |
| 2007/0066939 A1 | 3/2007 | Krulevitch et al. |
| 2007/0078382 A1 | 4/2007 | Hommann et al. |
| 2007/0142787 A1 | 6/2007 | Scherer |
| 2007/0156091 A1 | 7/2007 | Fathallah et al. |
| 2007/0156112 A1 | 7/2007 | Walsh |
| 2007/0208296 A1 | 9/2007 | Paproski et al. |
| 2008/0033395 A1 | 2/2008 | Alchas |
| 2008/0172024 A1 | 7/2008 | Yow |
| 2008/0213590 A1 | 9/2008 | Greiner et al. |
| 2008/0269680 A1 | 10/2008 | Ibranyan et al. |
| 2008/0306443 A1 | 12/2008 | Neer et al. |
| 2008/0312602 A1 | 12/2008 | Barrow-Williams et al. |
| 2008/0312606 A1 | 12/2008 | Harrison et al. |
| 2009/0036764 A1 | 2/2009 | Rivas et al. |
| 2009/0054849 A1 | 2/2009 | Burnell et al. |
| 2009/0088688 A1 | 4/2009 | Timothy Donald et al. |
| 2009/0209554 A1 | 8/2009 | Boyd et al. |
| 2009/0234297 A1 | 9/2009 | Jennings |
| 2010/0016793 A1 | 1/2010 | Jennings et al. |
| 2010/0036319 A1 | 2/2010 | Drake et al. |
| 2011/0092954 A1 | 4/2011 | Jennings |
| 2011/0098647 A1 | 4/2011 | Jennings |
| 2011/0098655 A1 | 4/2011 | Jennings et al. |
| 2011/0130743 A1 | 6/2011 | Jennings et al. |
| 2011/0282278 A1 | 11/2011 | Stamp et al. |
| 2012/0232491 A1 | 9/2012 | Jennings |
| 2012/0323177 A1 | 12/2012 | Adams et al. |
| 2013/0096512 A1 | 4/2013 | Ekman et al. |
| 2013/0267898 A1 | 10/2013 | Hourmand et al. |
| 2013/0317446 A1 | 11/2013 | Hourmand et al. |
| 2013/0331794 A1 | 12/2013 | Ekman et al. |
| 2013/0338601 A1 | 12/2013 | Cowe |
| 2013/0345643 A1 | 12/2013 | Hourmand et al. |

FOREIGN PATENT DOCUMENTS

| | | |
|---|---|---|
| CN | 1190599 A | 8/1998 |
| CN | 1420794 A | 5/2003 |
| CN | 1541121 A | 10/2004 |
| CN | 1550240 A | 12/2004 |
| CN | 101014379 A | 8/2007 |
| CN | 101068585 A | 11/2007 |
| DE | 902776 C | 1/1954 |
| DE | 229932 A1 | 11/1985 |
| DE | 3604826 A1 | 10/1986 |
| DE | 4428467 A1 | 2/1996 |
| DE | 29513214 U1 | 1/1997 |
| DE | 19603707 A1 | 8/1997 |
| DE | 69506521 T2 | 6/1999 |
| DE | 10137962 A1 | 2/2003 |
| DE | 10207276 A1 | 9/2003 |
| DE | 20311996 U1 | 10/2003 |
| EP | 0111724 B1 | 11/1983 |
| EP | 0096314 A2 | 12/1983 |
| EP | 0144625 A2 | 6/1985 |
| EP | 0240787 A2 | 3/1987 |
| EP | 0518416 A1 | 12/1992 |
| EP | 0331452 A2 | 8/1993 |
| EP | 0585626 A1 | 3/1994 |
| EP | 0389938 B1 | 5/1994 |
| EP | 0516473 B1 | 2/1996 |
| EP | 0482677 B1 | 4/1998 |
| EP | 0602883 B1 | 7/1998 |
| EP | 0857491 A1 | 8/1998 |
| EP | 0824922 B1 | 4/2002 |
| EP | 1260241 A1 | 11/2002 |
| EP | 0824923 B1 | 7/2003 |
| EP | 1228777 B1 | 10/2003 |
| EP | 0991441 B1 | 12/2003 |
| EP | 1166809 B1 | 3/2004 |
| EP | 0666084 B1 | 4/2004 |
| EP | 0941133 B1 | 4/2004 |
| EP | 1124601 B1 | 12/2004 |
| EP | 1364667 B1 | 4/2005 |
| EP | 1208858 B1 | 6/2006 |
| EP | 1755710 A1 | 2/2007 |
| EP | 1586341 B1 | 1/2008 |
| EP | 2023980 A1 | 2/2009 |
| EP | 2129414 A1 | 12/2009 |
| EP | 1755706 B1 | 3/2010 |
| EP | 1928523 B1 | 7/2010 |
| EP | 1518575 B1 | 11/2010 |
| EP | 1932558 B1 | 6/2011 |
| FR | 1014881 A | 8/1952 |
| FR | 1169935 A | 1/1959 |
| FR | 1538565 A | 9/1968 |
| FR | 2506161 A1 | 11/1982 |
| FR | 2629706 A | 10/1989 |
| FR | 2654938 A1 | 5/1991 |
| FR | 2665079 A1 | 1/1992 |
| FR | 2717086 A1 | 9/1995 |
| FR | 2741810 A1 | 6/1997 |

(56) References Cited

FOREIGN PATENT DOCUMENTS

| | | |
|---|---|---|
| FR | 2805868 A1 | 9/2001 |
| FR | 2830765 A1 | 4/2003 |
| FR | 2861310 A1 | 4/2005 |
| GB | 143084 | 5/1920 |
| GB | 0412054 | 6/1934 |
| GB | 728248 | 4/1955 |
| GB | 909898 | 11/1962 |
| GB | 1263355 | 2/1972 |
| GB | 1311937 A | 3/1973 |
| GB | 1514725 A | 6/1978 |
| GB | 2338033 A | 12/1999 |
| GB | 2388033 A | 11/2003 |
| GB | 2396298 A | 6/2004 |
| GB | 2396816 A | 7/2004 |
| GB | 2397767 A | 8/2004 |
| GB | 2404338 A | 2/2005 |
| GB | 2414398 A | 11/2005 |
| GB | 2414399 A | 11/2005 |
| GB | 2414400 A | 11/2005 |
| GB | 2414401 A | 11/2005 |
| GB | 2414402 A | 11/2005 |
| GB | 2414403 A | 11/2005 |
| GB | 2424835 A | 10/2006 |
| GB | 2424836 A | 10/2006 |
| GB | 2424837 A | 10/2006 |
| GB | 2424838 A | 10/2006 |
| GB | 2425062 A | 10/2006 |
| GB | 2433035 A | 6/2007 |
| GB | 2437922 A | 11/2007 |
| GB | 2438591 A | 12/2007 |
| GB | 2445090 A | 6/2008 |
| GB | 2446778 A | 8/2008 |
| GB | 2451663 A | 2/2009 |
| JP | 59-115053 A | 7/1984 |
| JP | 2-185261 A | 7/1990 |
| JP | 2-502971 T | 9/1990 |
| JP | H 02-299660 A | 12/1990 |
| JP | 11-501549 T | 2/1992 |
| JP | 5-161712 A | 6/1993 |
| JP | 6-209996 A | 8/1994 |
| JP | 6-508773 T | 10/1994 |
| JP | 6-327770 A | 11/1994 |
| JP | H 07-116224 A | 5/1995 |
| JP | 7-213610 A | 8/1995 |
| JP | 7-222799 A | 8/1995 |
| JP | 8-502180 T | 3/1996 |
| JP | 8-504354 T | 5/1996 |
| JP | 9-225029 A | 9/1997 |
| JP | 10-504474 T | 5/1998 |
| JP | 10-507935 A | 8/1998 |
| JP | 11-503637 T | 3/1999 |
| JP | 11-504536 T | 4/1999 |
| JP | 11-164887 T | 6/1999 |
| JP | 11-512332 T | 10/1999 |
| JP | 2000-126293 A | 5/2000 |
| JP | 2000-510021 T | 8/2000 |
| JP | 2001-046498 A | 2/2001 |
| JP | 2001-212237 A | 8/2001 |
| JP | 2002-500933 T | 1/2002 |
| JP | 2002-502296 A | 1/2002 |
| JP | 2002-095749 A | 4/2002 |
| JP | 2002-513547 T | 5/2002 |
| JP | 2002-526175 A | 8/2002 |
| JP | 2002-528182 T | 9/2002 |
| JP | 2002-532161 T | 10/2002 |
| JP | 2003-511105 T | 3/2003 |
| JP | 2003-532500 T | 11/2003 |
| JP | 2003-533288 A | 11/2003 |
| JP | 2004-533282 T | 11/2004 |
| JP | 2004-537376 A | 12/2004 |
| JP | 2005-508214 A | 3/2005 |
| JP | 2005-177503 A | 7/2005 |
| JP | 2004-33737 A | 8/2005 |
| JP | 2006-223858 A | 8/2006 |
| JP | 2008-284177 A | 11/2008 |
| NZ | 335985 A | 4/2001 |
| NZ | 573171 A | 11/2010 |
| NZ | 573350 A | 12/2010 |
| WO | WO 88/10129 A1 | 12/1988 |
| WO | WO 98/10129 A1 | 12/1988 |
| WO | WO 92/19296 A | 11/1992 |
| WO | WO 93/02186 A1 | 2/1993 |
| WO | WO 93/21986 A2 | 11/1993 |
| WO | WO 93/23098 A1 | 11/1993 |
| WO | WO 94/04207 A1 | 3/1994 |
| WO | WO 94/07554 A1 | 4/1994 |
| WO | WO 94/11041 | 5/1994 |
| WO | WO 94/13342 A1 | 6/1994 |
| WO | WO 94/21316 A1 | 9/1994 |
| WO | WO 94/22511 A1 | 10/1994 |
| WO | WO 95/04562 A1 | 2/1995 |
| WO | WO 95/29720 A1 | 11/1995 |
| WO | WO 95/31235 A1 | 11/1995 |
| WO | WO 95/35126 A1 | 11/1995 |
| WO | WO 95/35126 A1 | 12/1995 |
| WO | WO 96/30065 A1 | 10/1996 |
| WO | WO 97/10865 A1 | 3/1997 |
| WO | WO 97/13538 A1 | 4/1997 |
| WO | WO 97/48430 A1 | 12/1997 |
| WO | WO 98/11927 A1 | 3/1998 |
| WO | WO 99/03529 A2 | 1/1999 |
| WO | WO 99/10030 A2 | 3/1999 |
| WO | WO 99/22789 A1 | 5/1999 |
| WO | WO 99/37343 A | 7/1999 |
| WO | WO 99/53979 A1 | 10/1999 |
| WO | WO 99/59658 A1 | 11/1999 |
| WO | WO 00/06227 A1 | 2/2000 |
| WO | WO 00/07539 A1 | 2/2000 |
| WO | WO 00/13723 A2 | 3/2000 |
| WO | WO 00/24441 A1 | 5/2000 |
| WO | WO 00/35516 | 6/2000 |
| WO | WO 00/50107 A1 | 8/2000 |
| WO | WO 00/61209 | 10/2000 |
| WO | WO 00/64515 A1 | 11/2000 |
| WO | WO 00/69488 A2 | 11/2000 |
| WO | WO 01/05456 A1 | 1/2001 |
| WO | WO 01/49347 A1 | 7/2001 |
| WO | WO 01/60435 A1 | 8/2001 |
| WO | WO 01/76666 A1 | 10/2001 |
| WO | WO 01/77384 A2 | 10/2001 |
| WO | WO 01/87384 A1 | 11/2001 |
| WO | WO 02/11799 A1 | 2/2002 |
| WO | WO 02/47746 A2 | 6/2002 |
| WO | WO 02/056947 A1 | 7/2002 |
| WO | WO 02/074361 A2 | 9/2002 |
| WO | WO 03/013632 A2 | 2/2003 |
| WO | WO 03/015853 A1 | 2/2003 |
| WO | WO 03/039633 A2 | 5/2003 |
| WO | WO 03/041768 A | 5/2003 |
| WO | WO 03/047663 A2 | 6/2003 |
| WO | WO 03/051434 A2 | 6/2003 |
| WO | WO 03/066141 A1 | 8/2003 |
| WO | WO 03/092771 | 11/2003 |
| WO | WO 03/097133 | 11/2003 |
| WO | WO 03/099358 A2 | 12/2003 |
| WO | WO 2004/007554 A1 | 1/2004 |
| WO | WO 2004/011065 A1 | 2/2004 |
| WO | WO 2004/030732 A2 | 4/2004 |
| WO | WO 2004/035117 A2 | 4/2004 |
| WO | WO 2004/047890 A1 | 6/2004 |
| WO | WO 2004/047891 A1 | 6/2004 |
| WO | WO 2004/047892 A | 6/2004 |
| WO | WO 2004/054644 A1 | 7/2004 |
| WO | WO 2004/054645 A3 | 7/2004 |
| WO | WO 2004/087242 A1 | 10/2004 |
| WO | WO 2004/101025 A2 | 11/2004 |
| WO | WO 2004/108194 A1 | 12/2004 |
| WO | WO 2005/004961 A1 | 1/2005 |
| WO | WO 2005/009515 A1 | 2/2005 |
| WO | WO 2005/023341 A1 | 3/2005 |
| WO | WO 2005/025636 A2 | 3/2005 |
| WO | WO 2005/030301 A1 | 4/2005 |
| WO | WO 2005/035028 A1 | 4/2005 |
| WO | WO 2005/044345 A | 5/2005 |

(56) References Cited

FOREIGN PATENT DOCUMENTS

| WO | WO 2005/044347 A1 | 5/2005 |
|---|---|---|
| WO | WO 2005/058396 A1 | 6/2005 |
| WO | WO 2005/070481 A1 | 8/2005 |
| WO | WO 2005/082438 A1 | 9/2005 |
| WO | WO 2005/097238 A3 | 10/2005 |
| WO | WO 2005/105014 A2 | 11/2005 |
| WO | WO 2005/115507 A1 | 12/2005 |
| WO | WO 2005/115508 A1 | 12/2005 |
| WO | WO 2005/115509 A1 | 12/2005 |
| WO | WO 2005/115510 A1 | 12/2005 |
| WO | WO 2005/115512 A1 | 12/2005 |
| WO | WO 2005/115513 A1 | 12/2005 |
| WO | WO 2005/115514 A1 | 12/2005 |
| WO | WO 2005/115516 A1 | 12/2005 |
| WO | WO 2005/120607 A2 | 12/2005 |
| WO | 2006/008086 A1 | 1/2006 |
| WO | WO 2006/044236 A2 | 4/2006 |
| WO | WO 2006/050304 A1 | 5/2006 |
| WO | WO 2006/062788 A2 | 6/2006 |
| WO | WO 2006/063015 A2 | 6/2006 |
| WO | WO 2006/063124 A2 | 6/2006 |
| WO | WO 2006/088513 A1 | 8/2006 |
| WO | WO 2006/088630 A2 | 8/2006 |
| WO | WO 2006/099441 A2 | 9/2006 |
| WO | WO 2006/106290 A1 | 10/2006 |
| WO | WO 2006/106291 A1 | 10/2006 |
| WO | WO 2006/106292 A1 | 10/2006 |
| WO | WO 2006/106293 A1 | 10/2006 |
| WO | WO 2006/106294 A1 | 10/2006 |
| WO | WO 2006/106295 A1 | 10/2006 |
| WO | WO 2006/118616 A1 | 11/2006 |
| WO | WO 2006/129196 A1 | 12/2006 |
| WO | WO 2007/027204 A2 | 3/2007 |
| WO | WO 2007/036676 A1 | 4/2007 |
| WO | WO 2007/047200 A1 | 4/2007 |
| WO | WO 2007/051330 A1 | 5/2007 |
| WO | WO 2007/066152 A | 6/2007 |
| WO | WO 2007/122193 A1 | 11/2007 |
| WO | WO 2007/131013 A | 11/2007 |
| WO | WO 2007/138299 A1 | 12/2007 |
| WO | WO 2008/047372 A2 | 4/2008 |
| WO | WO 2008/075033 A | 6/2008 |
| WO | WO 2008/093063 A2 | 8/2008 |
| WO | WO 88/08725 | 11/2008 |

OTHER PUBLICATIONS

International Search Report dated Sep. 5, 2005; International Application No. PCT/GB2005/002117.
International Search Report dated May 30, 2006; International Application No. PCT/GB2005/003725.
International Search Report dated Sep. 9, 2005; International Application No. PCT/GB2005/002126.
Australian Search Report dated Dec. 6, 2007; Application No. SG 200608164-0.
International Search Report dated Sep. 5, 2005; International Application No. PCT/GB2005/002131.
Austrian Search Report dated Jan. 22, 2006; Application No. 200608166-5.
International Search Report dated Sep. 9, 2005; International Application No. PCT/GB2005/002120.
International Search Report dated Sep. 6, 2005; International Application No. PCT/GB2005/002108.
European Search Report dated Apr. 23, 2007; Application No. 06077332.2.
International Search Report dated Sep. 5, 2005; International Application No. PCT/GB2005/002105.
Singapore Search Report dated Feb. 26, 2008; Application No. 200608070-9.
International Search Report dated Sep. 5, 2005; International Application No. PCT/GB2005/002116.
International Search Report dated Sep. 5, 2005; International Application No. PCT/GB2005/002128.
Australian Search Report dated Dec. 11, 2007; Application No. 200608165-7.
International Search Report dated May 23, 2006; International Application No. PCT/GB2006/001017.
International Search Report dated May 29, 2006; International Application No. PCT/GB2006/001018.
International Search Report dated Jun. 2, 2006; International Application No. PCT/GB2006/001030.
International Search Report dated Jun. 1, 2006; International Application No. PCT/GB2006/001029.
International Search Report dated Sep. 9, 2005 International Application No. PCT/GB2005/002135.
International Search Report dated May 30, 2006; International Application No. PCT/GB2006/001031.
International Search Report dated Jun. 27, 2006; International Application No. PCT/GB2006/001023.
International Search Report dated Feb. 27, 2007; International Application No. PCT/IB2006/002792.
European Search Report dated Feb. 1, 2006; Application No. 05255298.1.
Great Britain Search Report dated Sep. 22, 2006; Application No. GB0610860.9.
International Search Report dated Aug. 22, 2007; International Application No. PCT/GB2007/001992.
International Search Report dated Sep. 4, 2007; International Application No. PCT/GB2007/002002.
Great Britain Search Report dated Sep. 28, 2006; Application No. GB0610859.1.
International Search Report dated Aug. 22, 2007; International Application No. PCT/GB2007/001973.
International Search Report dated Feb. 26, 2008; International Application No. PCT/GB2007/004335.
International Search Report dated Sep. 13, 2007; International Application No. PCT/GB2007/001999.
International Search Report dated Aug. 28, 2007; International Application No. PCT/GB2007/001969.
International Search Report dated Oct. 10, 2008; International Application No. PCT/GB2008/002578.
Great Britain Search Report dated Nov. 12, 2007; Application No. GB0715460.2.
International Search Report dated Oct. 14, 2008; International Application No. PCT/GB2008/002580.
Great Britain Search Report dated Nov. 12, 2007; Application No. GB0715459.4.
International Search Report dated Nov. 27, 2008; International Application No. PCT/GB2008/002579.
Great Britain Search Report dated Nov. 12, 2007; Application No. GB0715461.0.
International Search Report dated Oct. 10, 2008; International Application No. PCT/GB2008/002573.
Great Britain Search Report dated Nov. 12, 2007; Application No. GB0715456.0.
International Search Report dated Oct. 10, 2008; International Application No. PCT/GB2008/002583.
Great Britain Search Report dated Nov. 12, 2007; Application No. GB0715457.8.
International Search Report dated Sep. 30, 2009; International Application No. PCT/GB2009/001447.
Great Britain Search Report dated Sep. 25, 2008; Application No. GB0811348.2.
International Search Report dated Oct. 2, 2009; International Application No. PCT/GB2009/001448.
Great Britain Search Report dated Sep. 25, 2008; Application No. GB0811346.6.
International Search Report dated Oct. 5, 2009; International Application No. PCT/GB2009/001451.
Great Britain Search Report dated Sep. 25, 2008; Application No. GB0811347.4.
International Search Report dated Oct. 6, 2009; International Application No. PCT/GB2009/001453.
Great Britain Search Report dated Sep. 25, 2008; Application No. GB0811345.8.

(56) References Cited

OTHER PUBLICATIONS

International Search Report dated Oct. 5, 2009; International Application No. PCT/GB2009/001445.
Great Britain Search Report dated Sep. 25, 2008; Application No. GB0811349.0.
International Search Report dated Jan. 22, 2010; International Application No. PCT/GB2009/001446.
Great Britain Search Report dated Sep. 25, 2008; Application No. GB0811343.3.
International Search Report dated Jan. 12, 2008; International Application No. PCT/GB2008/002475.
Great Britain Search Report dated Nov. 16, 2007; Application No. GB0716774.5.
European Search Report dated Aug. 3, 2011; Application No. 11163779.9.
Singapore Search Report dated Mar. 15, 2012; Application No. SG 201007017-5.
European Search Report dated Jul. 20, 2011; Application No. 11163762.5.
Australian Search Report dated Feb. 26, 2008; Application No. SG 200608071-7.
International Search Report dated Sep. 5, 2005; International Application No. PCT/GB2005/002137.
European Search Report dated Feb. 28, 2011; Application No. 10179733.0.
European Search Report dated Mar. 4, 2011; Application No. 10179736.3.
European Search Report dated Jun. 16, 2011; Application No. 11160134.0.
European Search Report dated Apr. 17, 2012; International Application No. 12157660.7.
European Search Report dated Apr. 17, 2012; International Application No. 12157661.5.
European Search Report Dated Oct. 16, 2012; International Application No. 12177505.0.
European Search Report dated Aug. 4, 2011; Application No. 11169691.0.
Great Britain Search Report dated Sep. 29, 2006; Application No. GB0610856.7.
Great Britain Search Report dated Sep. 19, 2006; Application No. GB0610861.7.
European Search Report dated Oct. 15, 2013; Application No. 12182553.3.
Great Britain Search Report dated Dec. 9, 2013; Application No. GB1310394.0.
Great Britain Search Report dated Dec. 8, 2013; Application No. GB1310389.0.
Great Britain Search Report dated Dec. 9, 2013; Application No. GB1310402.1.
Great Britain Search Report dated Dec. 9, 2013; Application No. GB1310392.4.
Great Britain Search Report dated Dec. 10, 2013; Application No. GB1310393.2.
Great Britain Search Report dated Dec. 10, 2013; Application No. GB1310372.6.

\* cited by examiner

REUSABLE AUTO-INJECTOR

FIELD OF THE INVENTION

This invention relates to an injection device and, in particular, to a re-useable auto-injector device into which a drug may be transferred from a vial prior to subcutaneous injection into a patient.

BACKGROUND OF THE INVENTION

The use of automatic injection devices (commonly known as auto-injectors) to deliver a medicament to a patient has provided many benefits over manual syringes. In particular, auto-injectors have helped to relieve the burden on hospital staff to deliver a drug to a patient because patients are able to use the devices on themselves reliably and safely and in their own home.

Known auto-injectors are described in WO 95/35126 and EP-A-0 516 473. These and similar auto-injectors are typically provided primed (i.e. pre-sprung) and ready to be used for injecting a patient. For these reasons, it is difficult to insert a drug into the auto-injector and, as a consequence, manufacturers of such auto-injectors have typically provided a pre-filled syringe for use in the auto-injector, or a complete auto-injector unit which is pre-filled with a particular drug.

This requires a more complicated and expensive manufacturing process than would be otherwise required for an auto-injector because manufacturers must also obtain and provide the drugs and maintain the facilities for storing and handling them. Furthermore, the manufacturer must operate separate production lines for each drug which is required.

Drugs for medical use are often manufactured and distributed in standard vials. In this way, drugs may be supplied in bulk conveniently and relatively cheaply, regardless of the way in which the drug is finally used.

A significant cost-saving could be made in providing an auto-injector device which is capable of drawing a drug from a standard vial rather than relying on a pre-filled syringe. Not only would such a device benefit the manufacturers, who would no longer have to provide bespoke drug-filled devices, but also hospitals, which would enjoy a simplified inventory system and could make use of the standard vials which are used on a regular basis, and patients, who could be provided with a supply of vials for self administration.

In addition, the use of vials permits the possibility of reusing a greater proportion of an auto-injector device. Typically, auto-injectors are provided in two subassemblies. The first subassembly comprises the operating mechanisms and all other reusable components and the second subassembly contains the injection components that must be replaced each time the device is used.

A major factor in the cost of the second subassembly is the provision of a chamber which is pre-filled with a drug to be injected. As explained above, providing a range of syringes is an expensive and time-consuming aspect of the manufacturing process of an auto-injector. The use of standard vials would enable this cost to be reduced.

SUMMARY OF THE INVENTION

The present invention aims to solve the aforementioned problems. Accordingly, an injection device comprises a first sub-assembly comprising a chamber for holding a fluid, said chamber comprising an exit aperture and an inner surface; and a transfer assembly movably disposed within the chamber and having an outer surface substantially in contact with the inner surface about its perimeter, said transfer assembly being adapted to transfer fluid into the chamber when the transfer assembly is moved within the chamber.

Providing an injection device, such as an auto-injector, having a chamber into which a fluid may be transferred by a bespoke transfer assembly has at least two benefits over the prior art. Firstly, manufacturers of auto-injector devices need no longer manufacture a range of pre-filled syringes to be inserted into a reusable sub-assembly. Rather, the manufacturer may provide instead a single type of sub-assembly in accordance with the present invention into which any variety of drug may be transferred immediately prior to injection. The single type of sub-assembly may be manufactured in bulk, thereby reducing the manufacturing costs.

This advantage leads on to a second benefit whereby the invention may be used in conjunction with any type of container from which a drug may be transferred into the chamber. In particular the invention may be used with standard vials.

Furthermore, the invention allows a greater proportion of the needle assembly to be reused. Whereas known auto-injector systems require pre-filled syringes, the capability of transferring fluid into a chamber within the needle device permits greater scope for reusability.

The volume of the chamber into which the fluid is transferred is defined by the space between the distal end of the transfer assembly and the exit aperture. Consequently, the volume is increased as the stopper is moved away from the exit aperture. The increase in volume causes an initial decrease in pressure in the chamber which thereby draws the fluid into the chamber. Of course, in alternative embodiments, an increase in chamber volume, and a corresponding effect, may be achieved by moving the transfer assembly toward the exit aperture. Other embodiments which achieve an increase in chamber volume to draw fluid into the chamber are also envisaged.

Preferably, the transfer assembly is adapted to transfer fluid into the chamber when the transfer assembly is moved with respect to the chamber away from the exit aperture.

Optionally, the transfer assembly is adapted to receive a fluid container. In such an embodiment, the assembly may be further adapted to transfer fluid from the container into the chamber when it is moved, with respect to the chamber, away from the exit aperture. Using containers as a source of fluid provides additional benefits. It is straightforward to obtain, install and replace a container of fluid to be injected, and different fluids can be provided without any modification of the device. Other methods of providing a fluid source are contemplated, but inserting a fluid container directly into the transfer assembly is straightforward and reduces number of components required. Other approaches, such as providing a fluid pathway to a container situated elsewhere on the device, may provide additional benefits in terms of accessibility, for example.

Suitable containers may include any container configured to contain a drug and interface in some manner with the transfer assembly. Thus, a standard vial used to contain and transport fluid medicaments may be used in combination with this invention. In this manner, the cost of providing an auto-injector system is greatly reduced as the process of transferring the drug into a syringe may be performed entirely by the patient, and standard vials are easy to obtain and low in cost.

In certain embodiments, the transfer assembly may comprise a hollow fluid transfer needle adapted to engage the fluid container to form a fluid pathway from the container into the chamber through the hollow needle. Alternatively, the needle may comprise a fluid passageway including a unidirectional valve. This would enable transfer into, but not out of, the chamber.

Typically, containers used to contain drugs are provided with piercable foil or rubber caps. A hollow needle, provided on the transfer assembly and configured to pierce the cap, may form part of the fluid conduit between the container and the chamber. Of course, a needle is merely preferred. Other means may be provided according to the particular configuration of the container. For example, if the container were to comprise a valve, the means for transferring fluid into the chamber may comprise a hollow passage connected to the valve by a fluid tight seal. Other embodiments comprising a means for transferring fluid from the container are also envisaged.

Optionally, the transfer assembly may comprise a stopper for blocking fluid movement out of the transfer assembly. In such embodiments, the fluid transfer needle is adapted to pierce the stopper to deliver fluid through the stopper into the chamber. The stopper provides additional benefits in maintaining a seal between the transfer assembly and the chamber. It also prevents fluid from being transferred out of the chamber, other than through the exit aperture.

In certain embodiments, the transfer assembly includes a grip attached to the fluid transfer needle and movably disposed within the transfer assembly. The grip is adapted to move with the container as the container is inserted into the transfer assembly, thereby moving the fluid transfer needle into fluid communication with the chamber towards the exit aperture. Such embodiments improve the ease with which a fluid conduit between the container and the chamber is established. Preferably, the needle protrudes sufficiently from the grip to penetrate the cap of the container when the container is engaged with the transfer assembly. By pushing the container into the transfer assembly, the cap of the container may abut the grip and drive it, along with the needle, within the transfer assembly such that the needle pierces the stopper.

To secure a container when it is engaged with the transfer assembly, there may be provided a port having an opening adapted to receive and secure the container. The port is preferably situated at the opposite end of the transfer assembly to the end proximal the exit aperture.

In certain embodiments, the transfer assembly may be adapted to move away from the exit aperture within the chamber upon actuation of a mechanism, thereby drawing fluid into the chamber. Preferably, the mechanism is actuated by the user and the actuator in question is easily accessible on the device. More preferably, actuation is achieved by actuating part of a housing of the injector. In one embodiment, the transfer assembly is adapted to move away from the exit aperture upon rotation of the first sub-assembly. This actuation is merely preferred, however, and any mechanism which causes the transfer assembly to be moved within the chamber may be used.

In other embodiments, the injection device comprises a second sub-assembly. Optionally, the first sub-assembly and the transfer assembly are detachable from the second sub-assembly. Detachability enables certain parts of the device to be reused and others to be replaced. Preferably, the second sub-assembly is reusable. Whereas the first sub-assembly may comprise components which must be disposed of for hygiene reasons, or because they are spent, the second sub-assembly may comprise the drive mechanism which operates the needle device.

In the above embodiment, the transfer assembly may comprise a first thread and the second sub-assembly may comprise a second thread engageable with the first thread. The provision of the threads enables the first sub-assembly to be adapted to rotate with respect to the second sub-assembly. As a result of the rotation, the second sub-assembly moves the transfer assembly within the chamber away from the exit aperture.

In other embodiments, the transfer assembly is further adapted to expel fluid held within the chamber when the transfer assembly is moved toward the exit aperture.

BRIEF DESCRIPTION OF THE DRAWINGS

The invention will now be described by way of example with reference to the accompanying drawings, in which.

DETAILED DESCRIPTION OF THE DRAWINGS

Figure 1:
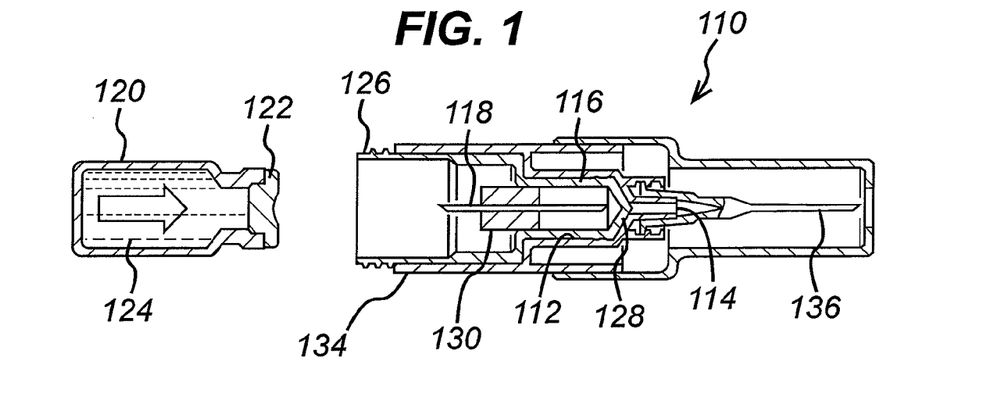
FIG. 1 is a side view of a first sub-assembly for use in an auto-injector according to the present invention.
Figure 2:
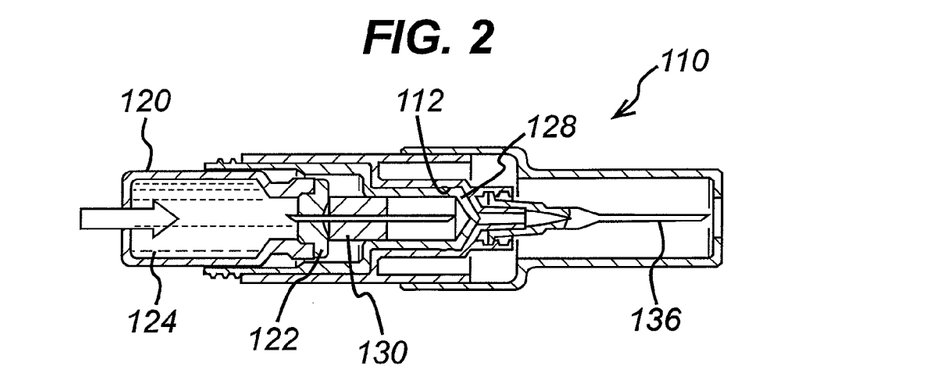
FIG. 2 is a side view of the first sub-assembly of FIG. 1 engaged with a vial.
Figure 3:
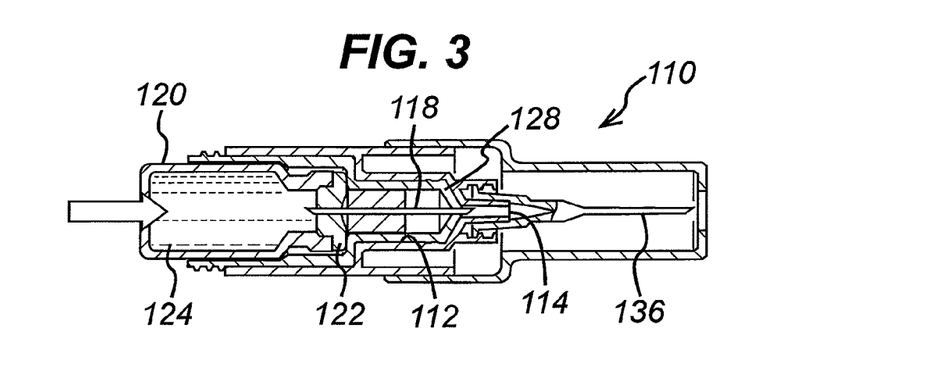
FIG. 3 is a second side view of the first sub-assembly engaged with the vial.

FIGS. 1 to 3 illustrate a first sub-assembly 110 of an injection device 100 according to the present invention.

The first sub-assembly 110 comprises a chamber 112 for holding a fluid. The chamber 112 comprises an exit aperture 114 and an inner surface. A transfer assembly 116 is moveably disposed within the chamber 112 and has an outer surface substantially in contact with the inner surface about its perimeter. The transfer assembly 116 is adapted to transfer fluid into the chamber when the transfer assembly 116 is moved within the chamber 112, as will be described in more detail below.

The first sub-assembly 110 further comprises a support structure 134 which defines the outer perimeter of the chamber 112 and contains the transfer assembly 116. The transfer assembly 116 is configured to move within the support structure 134.

In fluid communication with the exit aperture 114 is an injection needle 136. The injection needle is configured to pierce the skin of a patient and subcutaneously inject a fluid.

The transfer assembly 116 comprises proximal and distal ends. As depicted in FIG. 1, the distal end of the transfer assembly 116 is substantially in contact with the exit aperture 114.

At its proximal end, the transfer assembly comprises a port 126 adapted to receive a vial 120 comprising a cap 122 and containing a fluid 124. The port 126 is sized to accept the vial 120 and secure it within the transfer assembly 116.

At its distal end, the transfer assembly 116 comprises a stopper 128 for blocking fluid movement into and out of the transfer assembly 116. The stopper 128 is made out of rubber but other pliable materials may also be used.

The transfer assembly 116 further comprises a hollow fluid transfer needle 118. The transfer needle 118 extends from the port 126 to a position adjacent the stopper 128 and comprises proximal and distal ends configured to pierce the vial cap 120 and the stopper 128 respectively.

Surrounding the needle 118 and attached thereto is a grip 130. The grip 130, along with the needle 118, are moveable within the transfer assembly 116. As shown in FIG. 1, the grip 130 protrudes into the port 126.

FIG. 2 illustrates the first sub-assembly 110 engaged with the vial 120. As illustrated, the vial 120 has been engaged with the port 126 to enable the proximal end of the needle 118 to pierce the cap 122 of the vial 120, extend into the fluid 124, and form a first part of a fluid conduit between the vial 120 and the chamber 112.

Once engaged within the port, the cap 122 of the vial 120 abuts the grip 130 attached to the needle 118. The grip 130 is positioned on the needle 118 a sufficient distance from its proximal end to enable the needle 118 to pierce the cap 122 to gain access to the fluid.

As shown in FIG. 3, further engagement of the vial 120 causes the cap 122 to exert a force on the grip 130 and move it, along with the needle 118, through the transfer assembly 116. This movement causes the distal end of the needle 118 to pierce the stopper 128 to form a second part of the fluid conduit between the vial 120 and the chamber 112.

In this manner, engagement of the vial 120 with the transfer assembly 116 creates a complete fluid pathway between the vial 120 and the chamber 112, allowing fluid to be transferred there-between.

In the configuration of FIG. 3, the first sub-assembly 110 is adapted to transfer fluid from the vial 120 to the chamber 112. A fluid conduit exists, by virtue of the hollow needle which has pierced the cap and the stopper, between the vial 120 and the chamber 112. Movement of the transfer assembly 116 away from the exit aperture 114 of the chamber 112 will transfer fluid from the vial 120, through the needle and into the chamber 112.

FIGS. 4 to 8 show the engagement of the first sub-assembly 110 with a second sub-assembly 210. Once engaged, the two sub-assemblies form an auto-injector.

Figure 4:
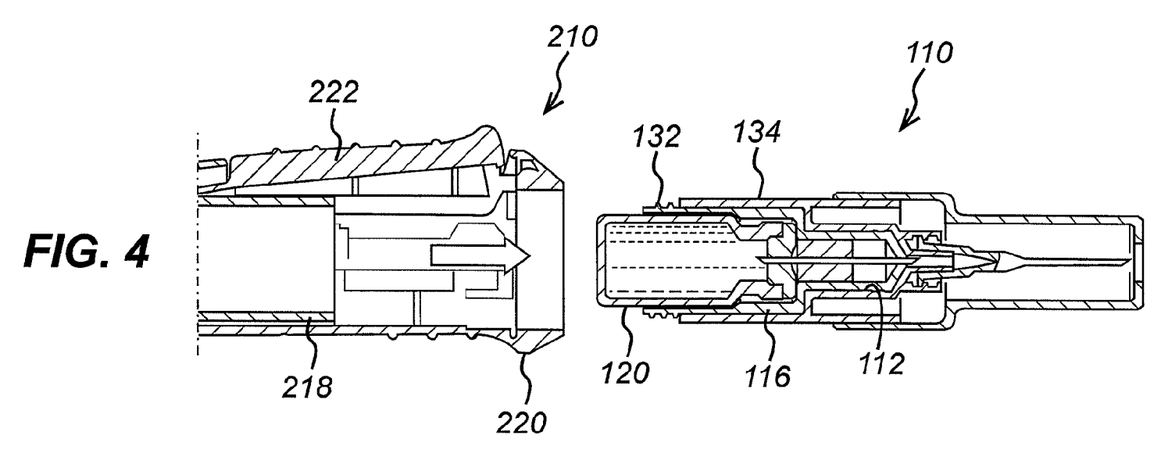
FIG. 4 is a side view of the first sub-assembly being engaged with a second sub-assembly for use in an auto-injector according to the present invention.

The second sub-assembly 210 comprises a housing 220 and a trigger mechanism 222. Within the housing 220 there is a drive means 212 comprising a spring 214, a drive rod 216 and an engagement mechanism 218 for engaging the transfer assembly 116 to transfer fluid from the vial 120 to the chamber 112.

As can be seen in FIG. 4, the transfer assembly 116 comprises a first thread 132 disposed on an outer surface of the assembly 116. The engagement mechanism 218 comprises a second thread (not shown) on an inner surface of the mechanism 218. The second thread is configured to be engageable with the first thread 132.

Figure 5:
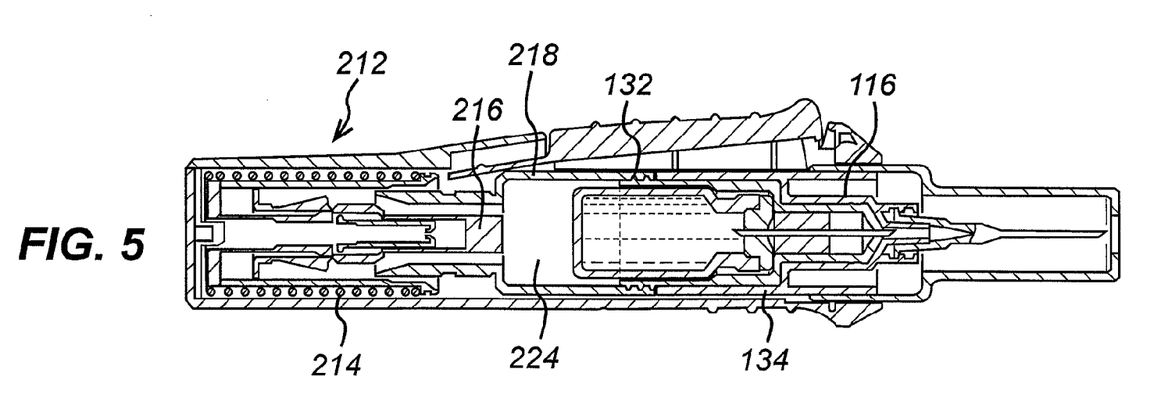
FIG. 5 is a side view of an auto-injector according to the present invention comprised of the first and second sub-assemblies.

The second sub-assembly 210 is engaged with the first sub-assembly 110 by sliding the first sub-assembly 110 within the second sub-assembly 210 through an opening at the distal end of the second sub-assembly. The vial 120 and the transfer assembly 116 are configured to fit within the engagement mechanism 218 to bring the first and second threads into engagement. To assist proper alignment, the proximal end of the support structure 134 is brought into contact with the distal end of the engagement mechanism 218 when the first and second sub-assemblies 110, 210 are fully engaged, as shown in FIG. 5.

A recess 224 in the engagement mechanism 218 provides a space into which the vial 120 and the transfer assembly may be moved to transfer fluid from the vial to the chamber. Movement is effected by rotation of the first sub-assembly 110 in relation to the second sub-assembly 210. Rotation of the first sub-assembly 110 causes the first thread of the transfer assembly 116 to rotate in relation to the second thread of the engagement mechanism 218, thereby moving the transfer assembly 116 away from the exit aperture of the chamber 112 into the recess 224 in the engagement mechanism 218.

Figure 6:
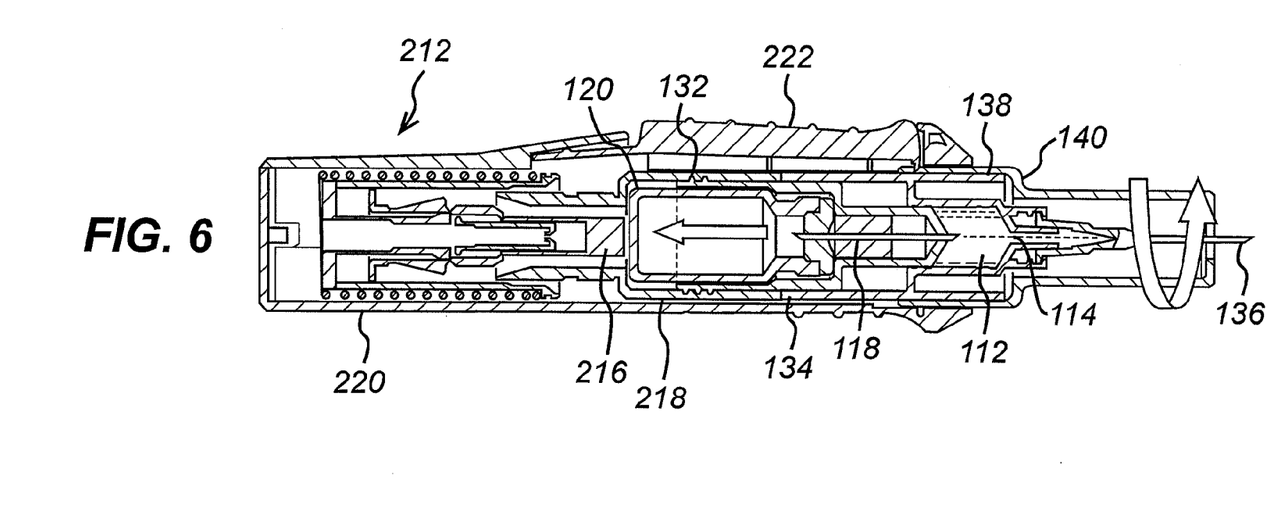
FIG. 6 is a side view of the auto-injector which has been primed by transferring fluid from the vial into the chamber.

FIG. 6 illustrates the injection device 100 wherein the transfer assembly 116 and the vial 120 have been retracted into the recess by virtue of the operation of the interconnecting first and second threads 132. As the transfer assembly 116 moves away from the exit aperture 114, the available volume of the chamber 112 increases. In the configuration depicted in FIG. 6, the chamber 112 is substantially at its maximum volume.

As the volume of the chamber increases, the pressure of that volume decreases, and the pressure difference between the vial and the chamber causes fluid to be drawn from the vial, through the needle into the chamber 112. As shown, the injection device 100 is primed to enable injection of the fluid from the chamber 112, through the exit aperture into a patient.

Figure 7:
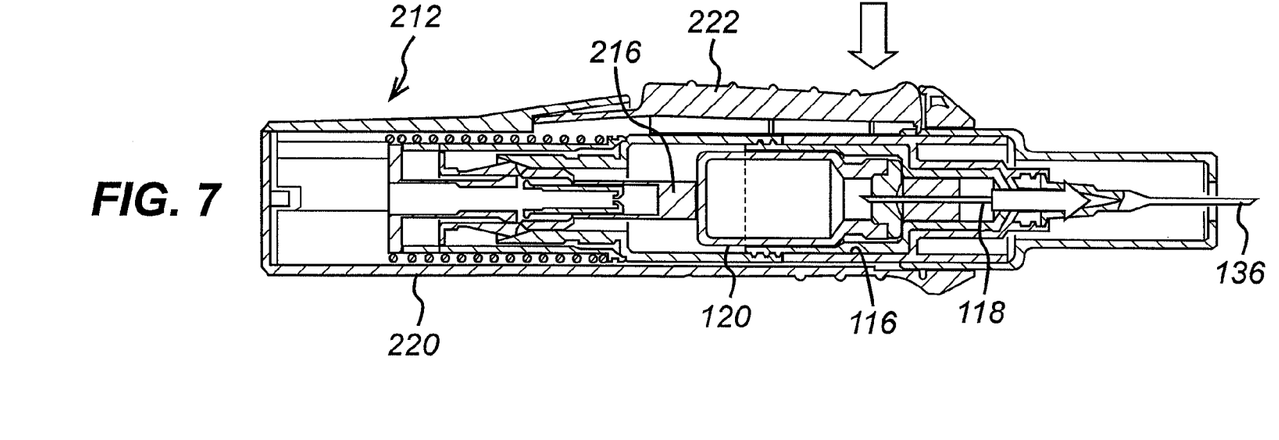
FIG. 7 is a side view of the auto-injector having been actuated to expose a needle and inject the fluid.
Figure 8:
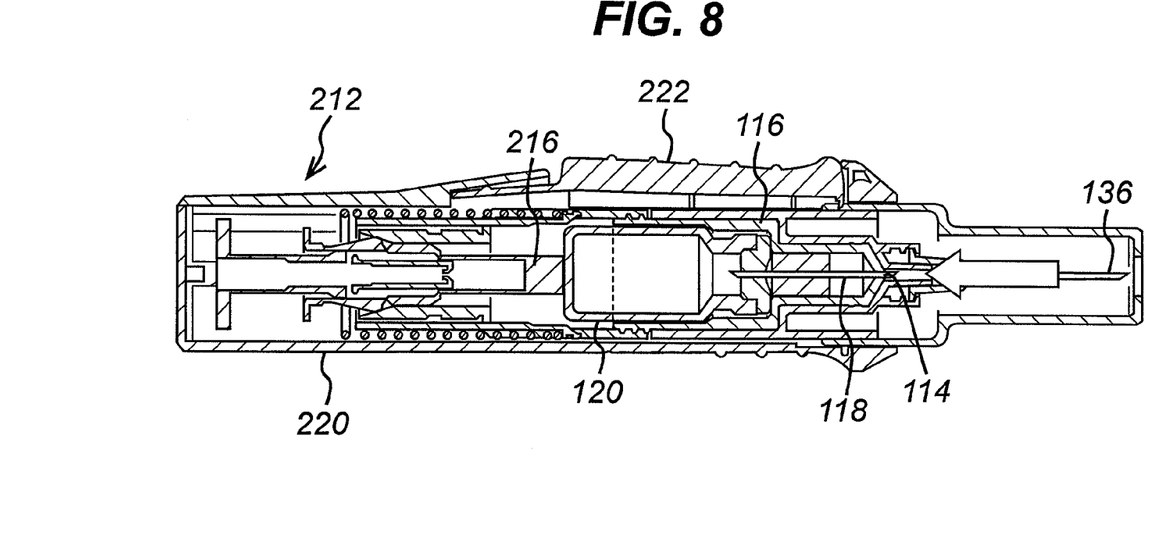
FIG. 8 is a side view of the auto-injector wherein the needle has been retracted following activation.

FIGS. 6 to 8 illustrate the injection of the fluid, having been transferred from the vial 120 to the chamber 112, from the chamber 112 to the patient.

The auto-injector comprises a trigger 222 configured to actuate the drive means 212. Upon actuation, the drive means 212 is configured to perform two distinct steps to inject the fluid into the patient. Firstly, the drive means is configured to extend the injection assembly (comprising the drive rod 216, the engagement mechanism 218, the transfer assembly 116, the vial 120, the support structure 134, the chamber 112, the exit aperture 112 and the delivery needle 136) toward the patient in relation to the housing 220. This step exposes at least part of the delivery needle 136 outside the housing 222, as shown in FIG. 6. The support structure 134 comprises an arm 138 which abuts a flange 140 of the first sub-assembly, to prevent the injection assembly from extending further than a desired point.

Secondly, the drive means is configured to drive the transfer assembly 116 towards the exit aperture 114. As the transfer assembly is moved, the available volume inside the chamber decreases and the fluid within the chamber 112 is forced out of the exit aperture 114. The force required to pass fluid through the exit aperture 114 is less than that required to pass fluid back into the transfer needle 118. Consequently, the fluid passes from the chamber 112, through the exit aperture 114 and the injection needle 136 into the patient.

As shown in FIG. 7, the second step is performed by the drive rod 216 which extends toward the patient in relation to the housing 220. The drive rod 216 contacts the vial 120 and drives it, along with the transfer assembly 116, through the chamber 112 to exert a pressure on the fluid in the chamber 112. When the pressure is sufficient, the fluid is driven out of the chamber 112, through the injection needle 136, into the patient.

Following injection of the fluid, the drive means 212 is configured to retract the needle assembly, including the needle 136, back into the housing, as depicted in FIG. 8.

Once the fluid has been injected, the second sub-assembly 210 may be disassembled from the first sub-assembly 110 and reused. The first sub-assembly 110 may be discarded and a new first sub-assembly 110 provided for subsequent injections, or may be sterilised for reuse.

It will be appreciated that modifications may be made to the embodiment described without departing from the scope of the invention, as defined in the appended claims.

The invention claimed is:
1. An injection device comprising:
a first sub-assembly comprising:

a chamber for holding a fluid, said chamber comprising an exit aperture and an inner surface; and a transfer assembly movably disposed within the chamber and having an outer surface substantially in contact with the inner surface about its perimeter, said transfer assembly being adapted to transfer fluid into the chamber when the transfer assembly is moved within the chamber;

wherein the transfer assembly is adapted to receive a fluid container and transfer fluid from the container into the chamber when the transfer assembly is moved with respect to the chamber;

wherein the transfer assembly comprises a hollow fluid transfer needle adapted to engage the fluid container to form a fluid pathway from the container into the chamber through the hollow needle;

wherein the transfer assembly further comprises a stopper for blocking fluid movement out of the transfer assembly; and wherein the fluid transfer needle is adapted to pierce the stopper to deliver fluid through the stopper into the chamber.

2. The injection device of claim 1, wherein the transfer assembly is adapted to transfer fluid into the chamber when the transfer assembly is moved with respect to the chamber away from its exit aperture.

3. The injection device of claim 1, further comprising a grip attached to the fluid transfer needle and movably disposed within the transfer assembly;

wherein the grip is adapted to move with the container as the container is inserted into the transfer assembly, thereby moving the fluid transfer needle into fluid communication with the chamber towards the exit aperture.

4. The injection device of claim 1, wherein the transfer assembly further comprises a port having an opening adapted to receive and secure the container at the opposite end to the exit aperture.

5. The injection device of any preceding claim, wherein the transfer assembly is adapted to move away from the exit aperture within the chamber upon rotation of the first sub-assembly, thereby drawing fluid into the chamber.

6. The injection device of claim 5, further comprising a second sub-assembly; wherein the transfer assembly comprises a first thread;

the second sub-assembly comprises a second thread engageable with the first thread; and the first sub-assembly is adapted to rotate with respect to the second sub-assembly and the second sub-assembly is adapted to move the transfer assembly within the chamber away from the exit aperture.

7. The injection device of any preceding claim, wherein the transfer assembly is further adapted to expel fluid held within the chamber when the transfer assembly is moved toward the exit aperture.

8. The injection device of any preceding claim, further comprising an injection needle in fluid communication with the exit aperture.

9. The injection device of claim 8 further comprising a releasable drive mechanism which, upon activation, is adapted to:

(a) move the chamber and the injection needle from a refracted position in which the needle is wholly inside a housing of the injection device to an extended position in which the needle is at least partially outside the housing; and (b) subsequently move the transfer assembly within the chamber toward the exit aperture to expel fluid out of the injection needle.

10. The injection device of claim 9, further comprising a refraction mechanism adapted to retract the injection needle into the housing after the fluid has been expelled.

11. The injection device of claim 6, wherein:

the first sub-assembly and the transfer assembly are detachable from the second sub-assembly; and the second sub-assembly is reusable.

\* \* \* \* \*